United States Patent
Mohr et al.

(10) Patent No.: US 7,026,264 B2
(45) Date of Patent: Apr. 11, 2006

(54) HYDROCARBON CONVERSION PROCESS AND CATALYST USEFUL THEREIN

(75) Inventors: Gary David Mohr, League City, TX (US); Wilfried Jozef Mortier, Kessel-lo (BE); Xiaobing Feng, League City, TX (US); Per Johan Sterte, Lulea (SE); Lubomira Borislavova Tosheva, Lulea (SE)

(73) Assignee: ExxonMobil Chemical Patents Inc., Houston, TX (US)

( * ) Notice: Subject to any disclaimer, the term of this patent is extended or adjusted under 35 U.S.C. 154(b) by 1 day.

(21) Appl. No.: 10/827,868

(22) Filed: Apr. 20, 2004

(65) Prior Publication Data

US 2004/0198586 A1 Oct. 7, 2004

Related U.S. Application Data

(60) Division of application No. 10/132,755, filed on Apr. 25, 2002, now Pat. No. 6,811,684, which is a continuation of application No. 09/574,433, filed on May 20, 2000, now abandoned.

(60) Provisional application No. 60/135,330, filed on May 20, 1999.

(51) Int. Cl.
*B01J 29/06* (2006.01)

(52) U.S. Cl. .................... 502/67; 502/60; 502/61; 502/63; 502/64; 502/66; 502/69; 502/71; 502/74; 502/77

(58) Field of Classification Search .............. 502/60, 502/61, 63, 64, 66, 67, 69, 71, 74, 77
See application file for complete search history.

(56) References Cited

U.S. PATENT DOCUMENTS

| | | | |
|---|---|---|---|
| 4,116,858 A | 9/1978 | Lee et al. | |
| 4,203,869 A | 5/1980 | Rollmann | |
| 4,472,332 A | 9/1984 | Fukushima et al. | |
| 4,477,583 A | 10/1984 | Rodewald | |
| 4,670,303 A | 6/1987 | Miles | |
| 4,680,170 A | 7/1987 | Loew et al. | |
| 4,847,224 A | 7/1989 | Fajula et al. | |
| 5,278,114 A | 1/1994 | Wielers et al. | |
| 5,753,121 A | 5/1998 | Geus et al. | |
| 5,851,378 A | 12/1998 | Vogt et al. | |
| 5,888,921 A | 3/1999 | Tsang et al. | |
| 5,981,052 A | 11/1999 | Sugiyama | |
| 5,993,642 A | 11/1999 | Mohr et al. | |
| 6,008,425 A | 12/1999 | Mohr et al. | |
| 6,037,292 A | 3/2000 | Lai et al. | |
| 6,040,259 A | 3/2000 | Mohr et al. | |
| 6,150,293 A | 11/2000 | Verduijn et al. | |
| 6,177,373 B1 | 1/2001 | Sterte et al. | |
| 6,198,013 B1 | 3/2001 | Mohr et al. | |
| 6,200,464 B1 | 3/2001 | van Houtert et al. | |
| 6,569,400 B1 * | 5/2003 | Sterte et al. | ............. 423/700 |
| 6,787,023 B1 * | 9/2004 | Mohr et al. | ................ 208/27 |
| 2002/0038775 A1 * | 4/2002 | Sterte et al. | ................ 208/59 |
| 2002/0192155 A1 * | 12/2002 | Sterte et al. | ............. 423/700 |
| 2003/0113248 A1 | 6/2003 | Mohr et al. | |
| 2003/0223933 A1 * | 12/2003 | Sterte et al. | ............. 423/716 |
| 2004/0045872 A1 * | 3/2004 | Sterte et al. | ......... 208/111.01 |

FOREIGN PATENT DOCUMENTS

| | | |
|---|---|---|
| EP | 0103035 | 3/1984 |
| EP | 0201264 | 12/1986 |
| EP | 0217143 | 4/1987 |
| EP | 0260826 | 10/1996 |
| WO | WO 8203571 | 10/1982 |
| WO | WO 9425151 | 11/1994 |
| WO | WO 9529751 | 11/1995 |
| WO | WO 96/07713 | 3/1996 |
| WO | WO 97/45198 | 12/1997 |
| WO | WO 0000287 | 1/2000 |

OTHER PUBLICATIONS

Tosheva, L. et al., "Silicate-1 containing microspheres prepared using shape-directing macro-templates," Microporous and Mesoporous Materials, US, Elsevier Science Publishing, New York, vol. 35-36, Apr. 2000, p. 621-629, XP004194501; ISSN: 1387-1811; the whole document.

* cited by examiner

*Primary Examiner*—Christina Johnson

(57) ABSTRACT

There is provided a process for converting hydrocarbons using a catalyst comprising macrostructures having a three-dimensional network of particles comprised of porous inorganic material. The particles of the macrostructures occupy less than 75% of the total volume of the macrostructures and are joined together to form a three-dimensional interconnected network comprised of pores having diameters greater than about 20 Å. The macrostructures can be made by forming an admixture containing a porous organic ion exchanger and a synthesis mixture capable of forming the porous inorganic material; converting the synthesis mixture to the porous inorganic material; and removing the porous organic ion exchanger from the inorganic material.

10 Claims, 5 Drawing Sheets

HYDROCARBON CONVERSION PROCESS AND CATALYST USEFUL THEREIN

CROSS-REFERENCE TO RELATED APPLICATIONS

This application is a divisional of U.S. application Ser. No. 10/132,755, filed Apr. 25, 2002 now U.S. Pat. No. 6,811,684, which is a continuation of U.S. application Ser. No. 09/574,433, filed May 20, 2000, now abandoned, and provisional U.S. application No. 60/135,330, filed May 20, 1999, each incorporated by reference.

FIELD OF THE INVENTION

This invention relates to hydrocarbon conversion using macrostructures of mesoporous or microporous inorganic material which can have controlled size, shape, and/or porosity.

BACKGROUND OF THE INVENTION

Both mesoporous inorganic material and micropborous inorganic material are characterized by a large specific surface area in pores and are used in a large number of applications of considerable commercial importance. In most of these applications, the fact that the phase interface between the solid porous materials and the medium (liquid or gas) in which it is used is large can be very important. For example, these porous inorganic materials are often used as catalysts and catalyst supports in hydrocarbon conversion processes. Also, these porous inorganic materials are often used as adsorbents for the selective adsorption in the gas or liquid phase or the selective separation of ionic compounds. As used herein, the terms "porous inorganic materials" and "porous materials" includes solid mesoporous inorganic material, solid microporous inorganic material, and mixtures thereof.

Although a large phase interface is often a fundamental requirement for use of porous materials in different applications, a number of additional requirements related to the particular area of application are imposed on these materials. For example, the large phase interface available in the pores of the porous inorganic material must be accessible and useable. In many applications, size and shape of the macrostructures containing the porous inorganic material and the degree of variation of these properties can be decisive importance. During use, the size and shape of the macrostructures can influence properties like mass transport within the structures, pressure drop over a bed of particles of the material, and the mechanical and thermal strength of the material. Techniques that permit production of a material with increased specific surface area, pore structure (pore size/pore size distribution), chemical composition, mechanical and thermal strength, as well as increased and uniform size and shape, are consequently required to tailor porous inorganic macrostructures to different applications.

Mesoporous inorganic materials include amorphous metal oxide (non-crystalline) materials which have mesoporous and optionally partially microporous structure. The pore size of the mesoporous inorganic material is usually in the range of from about 20 Å to about 500 Å.

Microporous inorganic materials include crystalline molecular sieves. The pore size of crystalline microporous molecular sieves is usually in the range of from about 2 Å to about 20 Å. Crystalline microporous molecular sieves, both natural and synthetic, such as zeolites, have been demonstrated to have catalytic properties for various types of hydrocarbon conversion processes. In addition, the crystalline microporous molecular sieves have been used as adsorbents and catalyst carriers for various types of hydrocarbon conversion processes, and other applications. These molecular sieves are ordered, porous, crystalline material having a definite crystalline structure as determined by x-ray diffraction, within which there are a large number of smaller cavities which may be interconnected by a number of still smaller channels or pores. The dimensions of these channels or pores are such as to allow adsorption of molecules with certain dimensions while rejecting those with larger dimensions. The interstitial spaces or channels formed by the crystalline network enable molecular sieves to be used as molecular sieves in separation processes and catalysts and catalyst supports in a wide variety of hydrocarbon conversion processes.

Molecular sieves can be classified into various groups by their chemical composition and their structure. One group of molecular sieves is commonly referred to as zeolites. Zeolites are comprised of a lattice of silica and optionally alumina combined with exchangeable cations such as alkali or alkaline earth metal ions. Although the term "zeolites" includes materials containing silica and optionally alumina, the silica and alumina portions may be replaced in whole or in part with other oxides. For example, germanium oxide, titanium oxide, tin oxide, phosphorous oxide, and mixtures thereof can replace the silica portion. Boron oxide, iron oxide, titanium oxide, gallium oxide, indium oxide, and mixtures thereof can replace the alumina portion. Accordingly, the terms "zeolite", "zeolites" and "zeolite material", as used herein, shall mean crystalline microporous molecular sieves including molecular sieves containing silicon and, optionally, aluminum atoms in the crystalline lattice structure thereof, molecular sieves which contain suitable replacement atoms for such silicon and aluminum and ALPO-based molecular sieves which contain framework tetrahedral units of alumina ($AlO_2$) and phosphorous oxide ($PO_2$) and, optionally, silica ($SiO_2$). Examples of ALPO-based molecular sieves include SAPO, ALPO, MeAPO, MeAPSO, ELAPO, and ELAPSO. The term "aluminosilicate zeolite", as used herein, shall mean zeolites consisting essentially of silicon and aluminum atoms in the crystalline lattice structure thereof.

Many times it is desirable to carry out hydrocarbon conversion processes using small particles, e.g., crystals. The term "small crystals", is used herein to mean the crystals have a diameter less than about 1 micron. For example, small crystal zeolites can have advantages over larger crystals when used as a catalyst, or catalyst base for reactions involving hydrocarbon conversion, because of their enhanced ratio of surface area to mass, high diffusion rates and reactivities, and resistance to deactivation by pore plugging and surface contamination. For similar reasons, they can have advantages in hydrocarbon separations.

Prior to using the porous inorganic material, especially crystalline microporous molecular sieves such as zeolites, in hydrocarbon conversion, the material is usually formed into structures, e.g., aggregates, such as pills, spheres, tablets, pellets, or extrudates. For example, although zeolite crystals have good adsorptive properties, their practical applications are very limited because it is difficult to operate fixed beds with zeolite powder. Therefore, prior to using the zeolite crystals in commercial processes, mechanical strength is conventionally conferred on the zeolite crystals by forming a zeolite aggregate such as a pill, sphere, or extrudate which usually is a dimension greater than 0.01 mm. The extrudate can be formed by extruding the zeolite crystals in the presence of a non-zeolitic binder and drying and calcining the resulting extrudate. The binder materials used are resistant to the temperatures and other conditions, e.g., mechanical attrition, which occur in various hydrocarbon conversion processes. It is generally necessary that the zeolite be resistant to mechanical attrition, that is, the formation of fines which are small particles, e.g., particles having a size of less than 20 microns. Examples of suitable binders include amorphous materials such as alumina, silica, titania, and various types of clays. Aggregates can also be formed without amorphous binder by compressing the crystals together in such a way that they become physically self bound.

Although such bound zeolite aggregates have much better mechanical strength than the zeolite powder, when the bound zeolite is used in a catalytic conversion process, the performance of the catalyst, e.g., activity, selectivity, activity maintenance, or combinations thereof, can be reduced because of the amorphous binder. For instance, since the binder is typically present in amounts of up to about 60 wt. % of the bound catalyst, the amorphous binder dilutes the adsorptive properties of the aggregate. In addition, since the bound zeolite is prepared by extruding or otherwise forming the zeolite with the amorphous binder and subsequently drying and calcining the extrudate, the amorphous binder can penetrate the pores of the zeolite or otherwise block access to the pores of the zeolite, or slow the rate of mass transfer to and from the pores of the zeolite which can reduce the effectiveness of the zeolite when used in hydrocarbon conversion processes and other applications. Furthermore, when a bound zeolite is used in catalytic conversion processes, the amorphous binder may affect the chemical reactions that are taking place within the zeolite and also may itself catalyze undesirable reactions which can result in the formation of undesirable products.

SUMMARY OF THE INVENTION

In one embodiment, the present invention is directed to the conversion of organic compounds under conversion conditions with a catalyst comprised of at least one macrostructure having a three-dimensional network of particles comprised of porous inorganic material. The particles of the macrostructures occupy less than 75% of the total volume of the macrostructures and are joined together to form a three-dimensional interconnected network comprised of pores having diameters greater than about 20 Å.

In another embodiment, the present invention is directed to the conversion of organic compounds under conversion conditions using the catalyst comprised of the at least one macrostructure having the three-dimensional interconnected network of particles, said catalyst made by a process which comprises the steps of: (a) forming an admixture containing the porous organic ion exchanger and a synthesis mixture capable of forming the porous inorganic material; (b) converting the synthesis mixture to the porous inorganic material; and (c) removing the porous organic ion exchanger.

In a further embodiment, the present invention is directed to macrostructures having particular application in the conversion of organic compounds and comprising the catalyst comprised of the at least one macrostructure having the three-dimensional interconnected network of particles that has a coating of porous inorganic material covering at least a portion of the external surface of the particles of the at least one macrostructure. The composition, structure type, or both of the coating can be the same or different from the microporous inorganic material of the macrostructures.

Examples of specific hydrocarbon conversion processes where the present invention finds particular application include catalytic cracking, alkylation, dealkylation, dehydrogenation, disproportionation, transalkylation, hydrocracking, isomerization, dewaxing, oligomerization, and reforming processes.

DETAILED DESCRIPTION OF THE INVENTION

Figure 1:
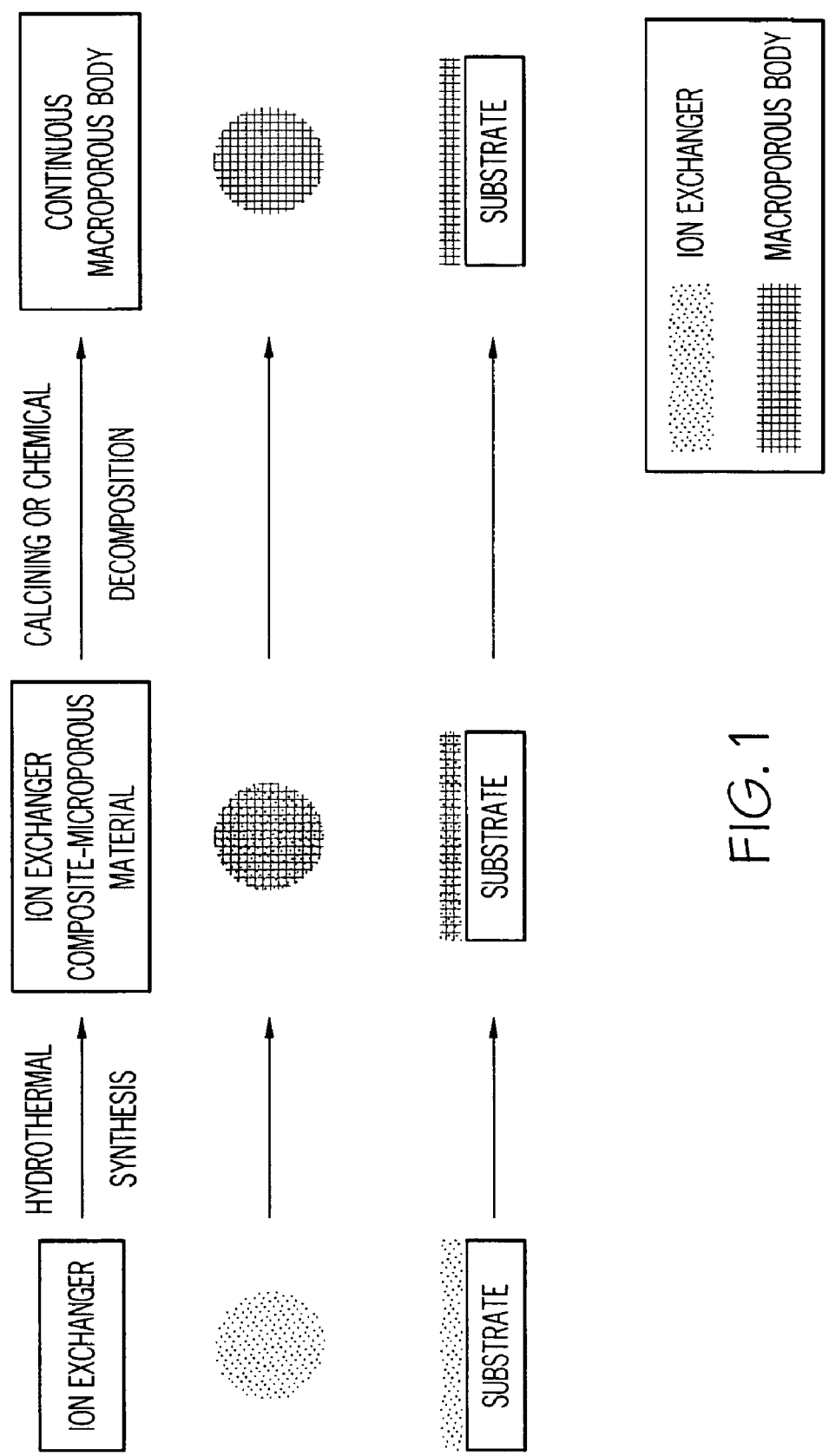
FIG. 1 represents a schematic description of the different stages of production of macrostructures used to carry out the present invention.

The term "macrostructures" means structures having a size that is greater than about 0.01 mm in at least one dimension, preferably greater than about 0.1 mm and, more preferably, greater than about 1.0 mm. The shape of macrostructures can be spherical, cylindrical, pellet, pill, fiber, or thin film applied to different forms of substrates and other composites, in which the porous material is combined with other types of material.

The term "average particle size" as used herein, means the arithmetic average of the diameter distribution of the particles on a volume basis. Procedures for determining the volume of the particles are known to persons skilled in the art. For instance, the volume of the particles can be calculated from SEM particle size measurements by taking into account the geometry of the particles. The term "particles" means the fundamental building blocks of the macrostructure material. In the case of crystalline molecular sieves, particles refers to crystals. In the case of other porous materials, particles refer the fundamental building blocks of these materials.

The macrostructure will be porous and will usually comprise a three-dimensional network (sometimes referred to as matrix) of particles of porous inorganic oxide. The macrostructures can be self supporting and are self bound. Usually, the particles will occupy less than 75% of the total volume of the macrostructures and may occupy less than 50% of the total volume of the macrostructure. The expression "total volume", as used herein, means the volume displaced by macrostructure material if all pores within the macrostructure were filled with non-porous material.

Usually, the particles will have an average particle size of less than 2 microns, and preferably less than 500 nm. More preferably, the particles will have an average particle size of less than 200 nm, e.g., 100 nm. The particles of the macrostructure will be joined together to form a three-dimensional interconnected network comprised of pores having diameters greater than about 20 Å. The network can be mesoporous, macroporous, or both. A macroporous network has pores greater than 500 Å. For example, with respect to macrostructures comprised of molecular sieve, where the molecular sieve has internal micropores of less than 20 Å in diameter, the network porosity is external to the particles. The porosity of the network may not be uniform. For example, the macrostructure may be combinations of mesoporous, macroporous, and hollow. Usually, the particles are joined together by means other than by physical binding of the particles. In most instances, the particles are joined together as a result of the synthesis of the macrostructure. Because of its high porosity, the macrostructure will usually have a density of less than 0.50 g/cc and in some instances, the density will be less than 0.45 g/cc. Procedures for determining the density, mesoporosity, microporosity, and particle size distribution of the macrostructure are know to persons skilled in the art. Examples of such procedures are described in *Handbook of Heterogeneous Catalyst* by G. Ertl, H. Knozinger, and J. Weitkamp (1997).

Porous inorganic materials that find application in the process of the present invention include crystalline molecular sieves (zeolites) and mesoporous materials. Examples of mesoporous material that find particular use include amorphous materials such as amorphous silica, amorphous alumina, amorphous aluminosilicates and mesoporous molecular sieves such as MCM-41 and MCM-48. For some applications, it is preferable that the pore size of the mesoporous inorganic material be in the range of from about 20 Å to about 50 Å.

Crystalline molecular sieves that find application include any of the naturally occurring or synthetic molecular sieves. Examples of these molecular sieves include large pore molecular sieves, intermediate pore size molecular sieves, and small pore molecular sieves. These molecular sieves and their isotypes are described in "Atlas of Zeolite Structure Types", eds. W. H. Meier, D. H. Olson and Ch. Baerlocher, Elsevier, Fourth Edition, 1996, which is hereby incorporated by reference. A large pore molecular sieve generally has a pore size of at least about 7 Å and includes LTL, VFI, MAZ, MEI, FAU, EMT, OFF, *BEA, BOG, and MOR structure type zeolites (IUPAC Commission of Zeolite Nomenclature). Examples of large pore molecular sieves include mazzite, offretite, zeolite L, VPI-5, zeolite Y, zeolite X, omega, Beta, ZSM-3, ZSM-4, ZSM-18, ZSM-20, MCM-9, SAPO-37, and ETS-10, ETAS-10, ETGS-10, and AM-6. An intermediate pore size molecular sieves generally has a pore size from about 5 Å to about 7 Å and includes, for example, MFI, MEL, MTW, EUO, MTT, MFS, AEL, AFO, HEU, FER, and TON structure type zeolites (IUPAC Commission of Zeolite Nomenclature). Examples of intermediate pore size molecular sieves include ZSM-5, ZSM-11, ZSM-12, ZSM-22, ZSM-23, ZSM-34, ZSM-35, ZSM-38, ZSM-48, ZSM-50, ZSM-57, MCM-22, MCM-36, MCM-49, MCM-56, MCM-68, silicalite 1, and silicalite 2. A small pore size molecular sieves has a pore size from about 3 Å to about 5.0 Å and includes, for example, CHA, ERI, KFI, LEV, and LTA structure type zeolites (IUPAC Commission of Zeolite Nomenclature). Examples of small pore molecular sieves include ZK-4, ZSM-2, SAPO-34, SAPO-35, ZK-14, SAPO-42, ZK-21, ZK-22, ZK-5, ZK-20, zeolite A, hydroxysodalite, erionite, chabazite, zeolite T., gmelinite, ALPO-17, and clinoptilolite.

The structure type of the molecular sieves and/or its composition will depend on its use. Macrostructures comprised of molecular sieves do not require the presence of significant amounts of amorphous binder materials to bind together the molecular sieves crystals. Thus, macrostructures comprised of molecular sieves crystals can contain less than 10% by weight of amorphous binder material based on the weight of the macrostructures. For many applications, these macrostructures will contain even lesser amounts of amorphous binder, e.g., 5% by weight and even less, e.g., the macrostructures can be substantially free of non-molecular sieve binder.

The molecular sieves, e.g., zeolites, can include silicates, metallosilicates such as aluminosilicates and gallosilicates, and ALPO-based molecular sieves such as alumino-phosphates (ALPO), silicoaluminophosphates (SAPO), metalloalumino-phosphates (MeAPO), and metalloaluminophospho-silicate. (MeAPSO)

When the zeolite is an crystalline metallosilicate, the chemical formula of anhydrous crystalline metallosilicate can be expressed in terms of moles as represented by the formula: $M_{2/n} O:W_2O_3:ZSiO_2$, wherein M is selected from the group consisting of proton, e, g, hydrogen, proton precursors, monovalent, divalent, and trivalent cations and mixtures thereof; n is the valence of the cation and Z is a number of at least 2, preferably at least 3, said value being dependent upon the particular type of molecular sieve, and W is a metal in the anionic framework structure of the molecular sieve such as aluminum, gallium, boron, or iron.

When the molecular sieve has an intermediate pore size, the molecular sieve preferably comprises a composition having the following molar relationship:

$$X_2O_3:(n)YO_2,$$

wherein X is a trivalent element, such as aluminum, gallium, titanium, iron, and/or boron, Y is a tetravalent element such as silicon, tin, and/or germanium; and n has a value greater than 10, usually 20 or greater, more usually from 50 to 2,000, said value being dependent upon the particular type of molecular sieve and the trivalent element present in the molecular sieve.

As known to persons skilled in the art, the acidity of a molecular sieve can be reduced using many techniques such as by dealumination and steaming. In addition, the acidity of a molecular sieve is dependent upon the form of the molecular sieve with the hydrogen form having the highest acidity and other forms of the molecular sieve such as the sodium form having less acidity than the acid form. Accordingly, the mole ratios of silica to alumina and silica to gallia disclosed herein shall include not only molecular sieves having the disclosed mole ratios, but shall also include molecular sieves not having the disclosed mole ratios but having equivalent catalytic activity.

When the molecular sieve is a gallosilicate intermediate pore size molecular sieve, the molecular sieve preferably comprises a composition having the following molar relationship:

$$Ga_2O_3:ySiO_2$$

wherein y is greater than about 20, typically from 20 to 200. The molecular sieve framework may contain only gallium and silicon atoms or may also contain a combination of gallium, aluminum, and silicon.

When the molecular sieve is an aluminosilicate molecular sieve, the silica to alumina mole ratio will usually depend upon the structure type of the molecular sieve and the particular hydrocarbon process in which the catalyst system is utilized and is therefore not limited to any particular ratio. Generally, however, and depending on the structure type of the molecular sieve, the molecular sieve will have a silica to alumina mole ratio of at least 2:1 and in some instances from 4:1 to about 7:1. For a number of molecular sieves, especially intermediate pore size molecular sieves, the silica to alumina mole ratio will be in the range of from about 10:1 to about 1,000:1 or even greater where the molecular sieve contains no more than trace amounts of alumina. For example, the molecular sieve can be silicalite, i.e., a MFI type substantially free of alumina, or silicalite 2, a MEL type substantially free of alumina. When the catalyst is utilized in acid catalyzed reactions such as cracking, the manufacture of paraxylene and benzene by the disproportionation of toluene, the alkylation of benzene or the like, the molecular sieve will be acidic and will preferably, when it is an intermediate pore size molecular sieve, have higher silica to alumina mole ratios, e.g., 20:1 to about 200:1.

The macrostructures used in the hydrocarbon conversion process of the present invention are preferably prepared by first forming a admixture comprising a synthesis mixture capable of forming said porous inorganic material and a porous organic ion exchanger. After forming the admixture, the said synthesis mixture is converted under hydrothermal conditions to form said porous inorganic material. The porous organic ion exchanger is then removed from the composite material.

More preferably, the macrostructures of porous organic material used in the process of the present invention are prepared by the following steps:

(a) forming a admixture comprising a porous organic ion exchanger and a synthesis mixture capable of forming said porous inorganic material and which occupies at least a portion of the pore space of the porous organic ion exchanger;

(b) converting said synthesis mixture under hydrothermal conditions to form said porous inorganic material; and, (c) removing said porous organic ion exchanger.

The porous organic ion exchanger can be removed using techniques know to persons skilled in the art. Examples of such techniques include oxidation processes such as calcination and chemical removal such as by chemical destruction or chemical dissolution. Usually, the removal of the porous organic ion exchanger will result in macrostructures with the size and shape of the pores of the employed organic ion exchanger.

It is also contemplated that macrostructures of porous organic material can be prepared by extruding the solid porous inorganic oxide material in the presence of a porous organic ion exchanger to form an aggregate and then removing the porous organic ion exchanger by an oxidation process, e.g., calcination, or by chemical dissolution.

The composition of the synthesis mixture will vary according to the porous inorganic material to be produced. For example, in making silicalite 1 or silicalite 2, the aqueous synthesis mixture will contain a source of silicon, and will usually contain a structure directing agent. When preparing an aluminosilicate molecular sieve, the aqueous synthesis mixture will contain sources of silica and alumina and will usually contain a structure directing agent. When the porous inorganic material to be produced is an ALPO-based molecular sieve, the aqueous synthesis mixture will contain sources of aluminum and phosphorus, optionally silicon and will usually contain a structure directing agent.

For the manufacture of a MFI structure type molecular sieve, especially ZSM-5 or silicalite, e.g., silicalite 1, the synthesis mixture is advantageously of a molar composition, calculated in terms of oxides, within the following ranges:

| | |
|---|---|
| $M_2O:SiO_2$ | 0 to 0.7 to:1 preferably 0.016 to 0.350:1 |
| $SiO_2:Al_2O_3$ | 12 to infinity:1 |
| $(TPA)_2O:SiO_2$ | 0 to 0.2:1 preferably 0 to 0.075:1 |
| $H_2O:SiO_2$ | 7 to 1000:1 preferably 9 to 300:1 | wherein TPA represents tetrapropylammonium and M is an alkali metal, preferably sodium or potassium, also Li, Cs and ammonia. Other template agents may be used in these ratios.

The organic ionic exchangers suitable for preparing the macrostructures are organic porous materials with a surface charge and ion exchange capacity for anions or cations. Preferably, the organic ionic exchangers are polymer-based which are sometimes referred to as ion exchange resins. Polymer-based ionic exchangers are commercially available or can be readily prepared from resins that are commercially available. Examples of such resins include resins sold by Rohm and Haas Company under the registered trademark Amberlyst and resins sold by the Dow Chemical Company under the registered trademark Dowex. These exchangers cover a broad spectrum of different cation and anion exchangers with varying ion exchange capacity, porosity, pore size and particle size. Ion exchangers with an apparent anion exchange capacity, typically greater than about 1 meq/gm of dry anion exchanger, are of special interest to the present invention. Macroreticular organic ionic exchangers are particularly preferred in the practice of the present invention. By "macroreticular" as the term is commonly used in the resin art, it is generally meant that the pores, voids, or reticules are substantially within the range of about 200 to about 2,000 Å. Macroreticular resins are also referred to as macroporous resins.

A preferred group of ion exchangers suitable for use in the process of the present invention are anion exchange resins comprising water-insoluble polymeric resins having attached thereto a plurality of active anion exchange sites. The resin generally contains sufficient of such active ion exchange groups to impart thereto a concentration of ion exchange sites in the range from about 0.5 to about 12 meq/gram dry resin, typically greater than 1 meq/gram, and in some cases, preferably from about 4 to about 5.5 meq/gram of dry resin.

Anion-exchange resins are characterized as either strong base or weak base anion-exchange resins depending on the active ion-exchange sites of the resin. Strong base anion-exchange resins consist of polymers having mobile monovalent anions, such as hydroxide and the like associated for example with covalently bonded quaternary ammonium, phosphonium or arsonium functional groups or tertiary sulfonium functional groups. These functional groups are known as active sites and are distributed over the surface of the resin particle. Strong base anion-exchange resins have the capacity to undergo ion exchange independent of the pH of the medium by virtue of their intrinsic ionic character. Macroreticular strong base anion-exchange resins in the hydroxide form are particularly preferred in the practice of the present invention.

The resin matrix of weak base anion-exchange resins contains chemically bonded thereto a basic, nonionic functional group. The functional groups include primary, secondary, or tertiary amine groups. These may be aliphatic, aromatic, heterocyclic or cycloalkane amine groups. They may also be diamine, triamine, or alkanolamine groups. The amines, for example, may include alpha, alpha'-dipyridyl, guanidine, and dicyanodiamidine groups. Other nitrogen-containing basic, non-ionic functional groups include nitrile, cyanate, isocyanate, thiocyanate, isothiocyanate, and isocyanide groups. Pyridine groups may also be employed.

Ion exchangers of the strongly basic type which contain quaternary ammonium groups, have been found to be particularly suited for use in the present invention. Commercially available ion exchangers are generally in the form of spherical particles with a relatively narrow particle size distribution. Organic ion exchangers with a size and shape other than spherical, for example, fibers or flakes, however, can be produced according to known techniques. It is also known that films of organic ion exchangers can be deposited on different forms of substrates.

The term "seeds" refers to particles, e.g., crystallites, of porous inorganic material, e.g., molecular sieves, that are capable of initiating crystallization of the desired porous inorganic material. The seeds, which can be present in the synthesis mixture before its synthesis, e.g., seeds can be added to the synthesis mixture, or can be formed in situ usually in the early stage of synthesis of the porous inorganic material and are characterized by the fact that by treatment of the synthesis mixture with appropriate concentration and under suitable conditions, the seeds can be made to grow and form individual particles, e.g., crystals, which may join together during the synthesis to form a macrostructure in the pore system of the ion exchanger. Examples of such seeds includes silicate seeds, metal silicate seeds such as aluminosilicate, borosilicate, gallosilicate, and iron silicate seeds, SAPO seeds, and ALPO seeds. Preferred seeds include olgomeric anions of silicates and metal silicates. The term "seeds" also includes microcrystals of porous inorganic material, e.g., crystals of molecular sieves with a size below 500 nm, e.g., 200 nm, and whose crystal structure can be identified by X-ray diffraction. Microcrystals of molecular sieves suitable for use in the process of the present invention are disclosed in U.S. Pat. No. 5,863,516, which is hereby incorporated by reference.

Although not intending to limit the invention in any way to any theory of operation, it is believed that one of the advantages of preparing the macrostructures using the porous organic ion exchanger is that the surface of the porous organic ion exchanger can facilitate nucleation of the synthesis mixture by causing the formation of seeds which can subsequently grow into a porous inorganic matrix. In line with this theory, it is believed that the surface charge of the porous organic ion exchanger can attract seeds or seed forming material onto the surface of the porous the ion exchanger. For example, anion exchange resins, which have a positive charge, can attract negatively charged seeds such as silicate seeds, metal silicate seeds and aluminosilicate seeds.

During the formation of the porous macrostructures using the porous organic ion exchanger, the seeds formed on or bonded to the surface in the organic ion exchanger are made to grow by hydrothermal treatment in an appropriate synthesis solution. Through this growth a continuous three-dimensional network of porous material is formed in the pore structure of the employed ion exchange structure. After this stage, the product is a composite material comprising two continuous three-dimensional networks, one comprising the polymer structure of the ion exchanger, and the second comprising the formed inorganic porous material. Introduction of seeds can be carried out physically in a separate stage, with a subsequent growth stage under hydrothermal conditions in a synthesis solution. However, it is also possible and often advantageous not to separate these stages, but instead to directly introduce the ion exchanger material into a synthesis solution and expose this to hydrothermal conditions, during which seeds are formed in or ion-exchanged from the synthesis solution to the ion exchanger, to then grow the material into a continuous structure.

The microporous molecular sieve or crystalline mesoporous inorganic material are generally produced by hydrothermal treatment of a synthesis mixture. Hydrothermal treatment refers to treatment in aqueous solution or aqueous suspension at a temperature exceeding 50° C., preferably exceeding 80° C. and, in most cases, exceeding 95° C. In some instances, it is preferable to carry out the hydrothermal treatment first at a lower temperature and then at a higher temperature. In the synthesis of some molecular sieves, e.g., silicalite 1, the crystallinity can be increased when the hydrothermal treatment is carried out in two steps. In the initial step, the temperature is lower, e.g., 90–110° C., than the second step, e.g., 150–165° C.

The composition of the mixture and the synthesis parameters, like temperature, time and pressure, can effect the product obtained was well as and the size and shape of the formed crystals. The material deposited in the pore system of the organic ion exchanger can vary depending on the composition of the synthesis mixture and the synthesis conditions. During crystallization of macrostructures of a given molecular sieve, it is sometimes desirable to use synthesis mixtures, which, in the absence of ion exchanger material, result in colloidal suspensions of the molecular sieve. In some instances, the ion exchanger material can influence the result of the synthesis.

After removal of the ion exchanger, the resulting inorganic macrostructure is usually very similar or even a replica in size and shape of the organic ion exchanger present in the synthesis admixture. The secondary pore structure of the macrostructure will usually remain following removal of the organic ion exchanger material. The macrostructure however, can be further treated after removal such as by deposition of the porous inorganic material on the macrostructure. For instance, molecular sieve can be deposited into a molecular sieve macrostructure, e.g., the secondary pore structure can be more or less filled and, in the extreme case, leave behind a homogeneous porous material. Also, microporous inorganic material, e.g., molecular sieve, can be deposited as a coating which covers at least a portion of the external surface of the particles, e.g., molecular sieve particles, contained within the macrostructure. The coating can have a composition, structure type, or both that is the same or different from the microporous inorganic material of the microstructure. Also, the coating can substantially coat the external surfaces of the macrostructure. The composition and/or structure type of the coating can be selected so that it is effective in reducing undesirable reactions on the surface of the macrostructure. For example, in shape selective reactions, such as disproportionation of toluene, a macrostructure comprising MFI type molecular sieve, e.g., ZSM-5, could be coated with silicalite 1 or silicalite 2 to reduce surface acid sites on the ZSM-5. One method of preparing these coated macrostructures comprises converting a molecular sieve synthesis solution in the presence of the macrostructures.

The porous inorganic material can be treated to provide a more acidic form or to replace at least in part the original metals present in macrostructure with a different cation, e.g., a Group IB to VIII Periodic Table metal. Such metals are known to persons skilled in the art and include, for example, one or more metals, and metals of Groups IIIA, IVA, VA, VIA, VIIA, VIII, IB, IIB, IIIB, IVB, and VB of the Periodic Table of the Elements. Examples of suitable metals include Group VIII metals (i.e., Pt. Pd, Ir, Rh, Os, Ru, Ni, Co, and Fe), Group IVA metals (i.e., Sn and Pb), Group VB metals (i.e., Sb and Bi), and Group VIIB metals (i.e., Mn, Tc, and Re). Noble metals (i.e., Pt, Pd, Ir, Rh, Os, and Ru) are sometimes preferred. Reference to the metal or metals is intended to encompass such metal or metals in the elemental state (i.e., zero valent) or in some other catalytically active form such as a n oxide, sulfide, halide, carboxylate, and the like.

The hydrocarbon conversion processes are used for processing hydrocarbon feedstocks. Hydrocarbon feedstocks contain carbon compounds and can be from many different sources, such as virgin petroleum fractions, recycle petroleum fractions, tar sand oil, and, in general, can be any carbon containing fluid susceptible to zeolitic catalytic reactions. Depending on the type of processing the hydrocarbon feed is to undergo, the feed can contain metal or can be free of metals. Also, the feed can also have high or low nitrogen or sulfur impurities.

The conversion of hydrocarbon feeds can take place in any convenient mode, for example, in fluidized bed, moving bed, or fixed bed reactors depending on the types of process desired.

The macrostructures by itself or in combination with one or more catalytically active substances can be used for a wide variety of hydrocarbon conversion processes. For example, the macrostructures can be bound into aggregates or compressed into large aggregate structures to form larger formed material. Also, the macrostructures can be used in combination with other catalysts such as bound zeolite catalysts, e.g., silica or alumina bound zeolite catalysts. Examples of hydrocarbon compound conversion processes that find application in the process of the present invention include, as non-limiting examples, the following:

(A) The catalytic cracking of a naphtha feed to produce light olefins. Typical reaction conditions include from about 500° C. to about 750° C., pressures of subatmospheric or atmospheric, generally ranging up to about 10 atmospheres (gauge) and residence time (volume of the catalyst feed rate) from about 10 milliseconds to about 10 seconds.

(B) The catalytic cracking of high molecular weight hydrocarbons to lower weight hydrocarbons. Typical reaction conditions for catalytic cracking include temperatures of from about 400° C. to about 700° C., pressures of from about 0.1 atmosphere (bar) to about 30 atmospheres, and weight hourly space velocities of from about 0.1 to about 100 hr-1.

(C) The transalkylation of aromatic hydrocarbons in the presence of polyalkylaromatic hydrocarbons. Typical reaction conditions include a temperature of from about 200° C. to about 500° C., a pressure of from about atmospheric to about 200 atmospheres, a weight hourly space velocity of from about 1 to about 100 hr-1 and an aromatic hydrocarbon/polyalkylaromatic hydrocarbon mole ratio of from about 0.5/1 to about 16/1.

(D) The isomerization of aromatic (e.g., xylene) feedstock components. Typical reaction conditions for such include a temperature of from about 230° C. to about 510° C., a pressure of from about 0.5 atmospheres to about 50 atmospheres, a weight hourly space velocity of from about 0.1 to about 200 hr-1 and a hydrogen/hydrocarbon mole ratio of from about 0 to about 100.

(E) The dewaxing of hydrocarbons by selectively removing straight chain paraffins. The reaction conditions are dependent in large measure on the feed used and upon the desired pour point. Typical reaction conditions include a temperature between about 200° C. and 450° C., a pressure up to 3,000 psig and a liquid hourly space velocity from 0.1 to 20.

(F) The alkylation of aromatic hydrocarbons, e.g., benzene and alkylbenzenes, in the presence of an alkylating agent, e.g., olefins, formaldehyde, alkyl halides and alcohols having 1 to about 20 carbon atoms. Typical reaction conditions include a temperature of from about 100° C. to about 500° C., a pressure of from about atmospheric to about 200 atmospheres, a weight hourly space velocity of from about 1 $hr^{-1}$ to about 100 $hr^{-1}$ and an aromatic hydrocarbon/alkylating agent mole ratio of from about 1/1 to about 20/1.

(G) The alkylation of aromatic hydrocarbons, e.g., benzene, with long chain olefins, e.g., $C_{14}$ olefin. Typical reaction conditions include a temperature of from about 50° C. to about 200° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1. The resulting products from the reaction are long chain alkyl aromatics which when subsequently sulfonated have particular application as synthetic detergents;

(H) The alkylation of aromatic hydrocarbons with light olefins to provide short chain alkyl aromatic compounds, e.g., the alkylation of benzene with propylene to provide cumene. Typical reaction conditions include a temperature of from about 10° C. to about 200° C., a pressure of from about 1 to about 30 atmospheres, and an aromatic hydrocarbon weight hourly space velocity (WHSV) of from 1 $hr^{-1}$ to about 50 $hr^{-1}$;

(I) The hydrocracking of heavy petroleum feedstocks, cyclic stocks, and other hydrocrack charge stocks. The catalytic macrostructure will contain an effective amount of at least one hydrogenation component of the type employed in hydrocracking catalysts.

(J) The alkylation of a reformate containing substantial quantities of benzene and toluene with fuel gas containing short chain olefins (e.g., ethylene and propylene) to produce mono- and dialkylates. Preferred reaction conditions include temperatures from about 100° C. to about 250° C., a pressure of from about 100 to about 800 psig, a WHSV-olefin from about 0.4 $hr^{-1}$ to about 0.8 $hr^{-1}$, a WHSV-reformate of from about 1 $hr^{-1}$ to about 2 $hr^{-1}$ and, optionally, a gas recycle from about 1.5 to 2.5 vol/vol fuel gas feed.

(K) The alkylation of aromatic hydrocarbons, e.g., benzene, toluene, xylene, and naphthalene, with-long chain olefins, e.g., $C_{14}$ olefin, to produce alkylated aromatic lube base stocks. Typical reaction conditions include temperatures from about 160° C. to about 260° C. and pressures from about 350 to 450 psig.

(L) The alkylation of phenols with olefins or equivalent alcohols to provide long chain alkyl phenols. Typical reaction conditions include temperatures from about 100° C. to about 250° C., pressures from about 1 to 300 psig and total WHSV of from about 2 $hr^{-1}$ to about 10 $hr^{-1}$.

(M) The conversion of light paraffins to olefins and/or aromatics. Typical reaction conditions include temperatures from about 425° C. to about 760° C. and pressures from about 10 to about 2000 psig. Processes for preparing aromatic compounds from light paraffins are described in U.S. Pat. No. 5,258,563, which is hereby incorporated by reference.

(N) The conversion of light olefins to gasoline, distillate and lube range hydrocarbons. Typical reaction conditions include temperatures of from about 175° C. to about 375° C. and a pressure of from about 100 to about 2000 psig.

(O) Two-stage hydrocracking for upgrading hydrocarbon streams having initial boiling points above about 200° C. to premium distillate and gasoline boiling range products or as feed to further fuels or chemicals In a first stage, the catalyst comprising one or more catalytically active substances, e.g., a Group VIII metal, and the effluent from the first stage would be reacted in a second stage using a second catalyst comprising one or more catalytically active substances, e.g., a Group VIII metal, as the catalyst. Typical reaction conditions include temperatures from about 315° C. to about 455° C., a pressure from about 400 to about 2500 psig, hydrogen circulation of from about 1000 to about 10,000 SCF/bbl and a liquid hourly space velocity (LHSV) of from about 0.1 to 10.

(P) A combination hydrocracking/dewaxing process in the presence of the catalytic macrostructure comprising a hydrogenation component and zeolite such as zeolite Beta. Typical reaction conditions include temperatures from about 350° C. to about 400° C., pressures from about 1400 to about 1500 psig, LHSVs from about 0.4 to about 0.6 and a hydrogen circulation from about 3000 to about 5000 SCF/bbl.

(Q) The reaction of alcohols with olefins to produce mixed ethers, e.g., the reaction of methanol with isobutene and/or isopentene to provide methyl-t-butyl ether (MTBE) and/or t-amyl methyl ether (TAME). Typical conversion conditions include temperatures from about 20° C. to about 200° C., pressures from 2 to about 200 atm, WHSV (gram-olefin per hour gram-catalyst) from about 0.1 $hr^{-1}$ to about 200 $hr^{-1}$ and an alcohol to olefin molar feed ratio from about 0.11/to about 5/1.

(R) The disproportionation of aromatics, e.g., the disproportionation of toluene to make benzene and paraxylene and the disproportionation of cumene to make benzene and diisopropylbenzene. Typical reaction conditions include a temperature of from about 200° C. to about 760° C., a pressure of from about atmospheric to about 60 atmosphere (bar), and a WHSV of from about 0.1 $hr^{-1}$ to about 30 $hr^{-1}$.

(S) The conversion of naphtha (e.g., $C_6$–$C_{10}$) and similar mixtures to highly aromatic mixtures. Thus, normal and slightly branched chained hydrocarbons, preferably having a boiling range above about 40° C., and less than about 200° C., can be converted to products having a substantial higher octane aromatics content by contacting the hydrocarbon feed with the catalytic macrostructure at a temperature in the range of from about 400° C. to 600° C., preferably 480° C. to 550° C. at pressures ranging from atmospheric to 40 bar, and liquid hourly space velocities (LHSV) ranging from 0.1 to 15.

(T) Selectively separating hydrocarbons by adsorption of the hydrocarbons. Examples of hydrocarbon separation include xylene isomer separation and separating olefins from a feed stream containing olefins and paraffins.

(U) The conversion of oxygenates, e.g., alcohols, such as methanol, or ethers, such as dimethylether, or mixtures thereof to hydrocarbons including olefins and aromatics with reaction conditions including a temperature of from about 275° C. to about 600° C., a pressure of from about 0.5 atmosphere to about 50 atmospheres and a liquid hourly space velocity of from about 0.1 to about 100;

(V) The oligomerization of straight and branched chain olefins having from about 2 to about 5 carbon atoms. The oligomers which are the products of the process are medium to heavy olefins which are useful for both fuels, i.e., gasoline or a gasoline blending stock, and chemicals. The oligomerization process is generally carried out by contacting the olefin feedstock in a gaseous state phase with a catalytic macrostructure at a temperature in the range of from about 250° C. to about 800° C., a LHSV of from about 0.2 to about 50 and a hydrocarbon partial pressure of from about 0.1 to about 50 atmospheres. Temperatures below about 250° C. may be used to oligomerize the feedstock when the feedstock is in the liquid phase when contacting the catalytic macrostructure. Thus, when the olefin feedstock contacts the catalyst in the liquid phase, temperatures of from about 10° C. to about 250° C. may be used.

(W) The conversion of $C_2$ unsaturated hydrocarbons (ethylene and/or acetylene) to aliphatic $C_{6-12}$ aldehydes and converting said aldehydes to the corresponding $C_{6-12}$ alcohols, acids, or esters.

In general, the catalytic conversion conditions include a temperature of from about 100° C. to about 760° C., a pressure of from about 0.1 atmosphere (bar) to about 200 atmospheres (bar), a weight hourly space velocity of from about 0.08 $hr^{-1}$ to about 2,000 $hr^{-1}$.

The process of the present invention finds application in the vapor phase disproportionation of toluene. Such vapor phase disproportionation comprises contacting toluene under disproportionation conditions with the macrostructures comprising large pore or intermediate pore size molecular sieves to yield a product mixture which comprises a mixture of unreacted (unconverted) toluene and benzene and xylene. In the more preferred embodiment, the catalyst will be first selectivated prior to use in the disproportionation process. Processes for selectivating the catalyst are known to persons skilled in the art. For instance, selectivation may be accomplished by exposing the catalyst in a reactor bed to a thermally decomposable organic compound, e.g., toluene, at a temperature in excess of the decomposition temperature of said compound, e.g., from about 480° C. to about 650° C., more preferably 540° C. to 650° C., at a WHSV in the range of from about 0.1 to 20 lbs of feed per pound of catalyst per hour, at a pressure in the range of from about 1 to 100 atmospheres, and in the presence of 0 to about 2 moles of hydrogen, more preferably from about 0.1 to about 2 moles of hydrogen per mole of organic compound, and optionally in the presence of 0–10 moles of nitrogen or another inert gas per mole of organic compound. This process is conducted for a period of time until a sufficient quantity of coke has deposited on the catalyst surface, generally at least about 2% by weight and more preferably from about 8 to about 40% by weight of coke. In a preferred embodiment, such a selectivation process is conducted in the presence of hydrogen in order to prevent rampant formation of coke on the catalyst.

Selectivation of the catalyst can also be accomplished by treating the catalyst with a selectivation agent such as an organosilicon compound. The silica compounds may comprise polysiloxane including silicone and siloxanes, and a silane including disilanes and alkoxysilanes.

Silicone compounds that find particular application can be represented by the formula:

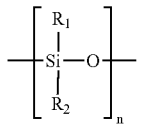

wherein $R_1$ is hydrogen, fluoride, hydroxy, alkyl, aralkyl, alkaryl or fluoro-alkyl. The hydrocarbon substituents generally contain from 1 to 10 carbon atoms and preferably are methyl or ethyl groups. $R_2$ is selected from the same group as $R_1$, and n is an integer of at least 2 and generally in the range of 2 to 1000. The molecular weight of the silicone compound employed is generally between 80 and 20,000 and preferably 150 to 10,000. Representative silicone compounds included dimethylsilicone, diethylsilicone, phenylmethylsilicone, methyl hydrogensilicone, ethylhydrogensilicone, phenylhydrogensilicone, methylethylsilicone, phenylethylsilicone, diphenylsilicone, methyltri fluoropropylsilicone, ethyltrifluoropropylsilicone, tetrachlorophenyl methyl silicone, tetrachlorophenylethyl silicone, tetrachloro phenylhydrogen silicone, tetrachlorophenylphenyl silicone, methylvinylsilicone and ethylvinylsilicone. The silicone compound need not be linear but may be cyclic as for example hexamethylcyclotrisiloxane, octamethylcyclotetrasiloxane, hexaphenyl cyclotrisiloxane and octaphenylcyclotetrasiloxane. Mixtures of these compounds may also be used as well as silicones with other functional groups.

Useful siloxanes or polysiloxanes include as non-limiting examples hexamethylcyclotrisiloxane, octamethylcyclotetrasiloxane, decamethyl cyclopentasiloxane, hexamethyldisiloxane, octamethytrisiloxane, decamethyltetrasiloxane, hexaethylcyclotrisiloxane, octaethylcyclo tetrasiloxane, hexaphenylcyclotrisiloxane and octaphenylcyclo tetrasiloxane.

Useful silanes, disilanes, or alkoxysilanes include organic substituted silanes having the general formula:

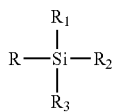

wherein R is a reactive group such as hydrogen, alkoxy, halogen, carboxy, amino, acetamide, trialkylsilyoxy, $R_1$, $R_2$, and $R_3$ can be the same as R or can be an organic radical which may include alkyl of from 1 to 40 carbon atoms, alkyl or aryl carboxylic acid wherein the organic portion of the alkyl contains 1 to 30 carbon atoms and the aryl group contains 6 to 24 carbon which may be further substituted, alkylaryl and arylalkyl groups containing 7 to 30 carbon atoms. Preferably, the alkyl group for an alkyl silane is between 1 and 4 carbon atoms in chain length.

When used for the vapor phase disproportionation of toluene, the catalytic macrostructures will preferably comprise aluminosilicate MFI-type zeolite having a silica to alumina mole ratio of from about 20 to about 200:1, preferably, 25:1 to about 120:1.

Once the catalyst has been selectivated to the desired degree, reactor selectivation conditions are changed to disproportionation conditions. Disproportionation conditions include a temperature between about 375° C. and 550° C., more preferably between about 400° C. and 485° C., at a hydrogen to toluene mole ratio of from 0 to about 10, preferably between about 0.1 and 5 and more preferably from about 0.1 to 1, at a pressure between about 1 atmosphere and 100 atmospheres and utilizing WHSV of between about 0.5 and 50.

The disproportionation process may be conducted as a batch, semi-continuous or continuous operation using a fixed or moving bed catalyst system deposited in a reactor bed. The catalyst may be regenerated after coke deactivation by burning off the coke to a desired extent in an oxygen-containing atmosphere at elevated temperatures as known in the art.

The process of the present invention also finds application in a process for isomerizing one or more xylene isomers in a $C_8$ aromatic feed to obtain ortho-, meta-, and para-xylene in a ratio approaching the equilibrium value. In particular, xylene isomerization is used in conjunction with a separation process to manufacture para-xylene. For example, a portion of the para-xylene in a mixed $C_8$ aromatics stream may be recovered using processes known in the art, e.g., crystallization, adsorption, etc. The resulting stream is then reacted under xylene isomerization conditions to restore ortho-, meta-, and paraxylenes to a near equilibrium ratio. Ethylbenzene in the feed is either removed from the stream or is converted during the process to xylenes or to benzene which are easily separated by distillation. The isomerate is blended with fresh feed and the combined stream is distilled to remove heavy and light by-products. The resultant $C_8$ aromatics stream is then recycled to repeat the cycle.

In the vapor phase, suitable isomerization conditions include a temperature in the range 250° C.–600° C., preferably 300° C.–550° C., a pressure in the range 0.5–50 atm abs, preferably 10–25 atm abs, and a weight hourly space velocity (WHSV) of 0.1 to 100, preferably 0.5 to 50. Optionally, isomerization in the vapor phase is conducted in the presence of 0.1 to 30.0 moles of hydrogen per mole of alkylbenzene.

When use to isomerize feeds containing ethylbenzene, the catalytic macrostructure catalyst will preferably contain at least one hydrogenation metal. Examples of such metals include the oxide, hydroxide, sulfide, or free metal (i.e., zero valent) forms of Group VIII metals (i.e., Pt, Pd, Ir, Rh, Os, Ru, Ni, Co, and Fe), Group IVA metals (i.e., Sn and Pb), Group VA metals (i.e., Sb and Bi), and Group VIIB metals (i.e., Mn, Tc, and Re). Noble metals (i.e., Pt, Pd, Ir, Rh, Os, and Ru) are preferred. Combinations of catalytic forms of noble or non-noble metals, such as combinations of Pt with Ni, may be used. The valence state of the metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

The amount of metal present in the catalyst will be an effective amount which will generally be from about 0.001 to about 10 percent by weight and, preferably 0.05 to 3.0 percent by weight.

The process of the present invention is useful for cracking a naphtha feed, e.g., $C_4^+$ naphtha feed, particularly a $C_4^-$ 290° C. naphtha feed to produce low molecular weight olefins, e.g., $C_2$ through $C_4$ olefins, particularly ethylene and propylene. Such a process is preferably carried out by contacting the naphtha feed at temperatures ranging from 500° C. to about 750° C., more preferably 550° C. to 675° C., at a pressure from subatmospheric up to 10 atmospheres, but preferably from about 1 atmosphere to about 3 atmospheres.

The process of the present invention is useful in the transalkylation of polyalkylaromatic hydrocarbons. Examples of suitable polyalkylaromatic hydrocarbons include di-, tri-, and tetra-alkyl aromatic hydrocarbons, such as diethylbenzene, triethylbenzene, diethylmethylbenzene (diethyl-toluene), diisopropyl-benzene, triisopropylbenzene, diisopropyltoluene, dibutylbenzene, and the like. Preferred polyalkylaromatic hydro-carbons are the dialkyl benzenes. Particularly preferred polyalkyl-aromatic hydrocarbons are diisopropylbenzene and diethylbenzene.

The feed used in the transalkylation process will preferably have a molar ratio of aromatic hydrocarbon to polyalkylaromatic hydrocarbon of preferably from about 0.5:1 to about 50:1, and more preferably from about 2:1 to about 20:1. The reaction temperature will preferably range from about 340° C. to 500° C. to maintain at least a partial liquid phase, and the pressure will be preferably in the range of about 50 psig to 1,000 psig, preferably 300 psig to 600 psig. The weight hourly space velocity will range from about 0.1 to 10.

The process of the present invention is also useful for converting aromatic compounds from paraffins. Example of suitable paraffins including aliphatic hydrocarbons containing 2 to 12 carbon atoms. The hydrocarbons may be straight chain, open or cyclic and may be saturated or unsaturated. Example of hydrocarbons include propane, propylene, n-butane, n-butenes, isobutane, isobutene, and straight- and branch-chain and cyclic pentanes, pentenes, hexanes, and hexenes.

The aromatization conditions include a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The catalytic macrostructure used in the aromatization process preferably comprises intermediate pore size zeolite such a MFI type zeolite (example ZSM-5). The catalyst preferably contains gallium. Gallium may be incorporated into the during synthesis of the macrostructure it may be exchanged or impregnated or otherwise incorporated into the macrostructure after synthesis. Preferably, 0.05 to 10, and most preferably 0.1 to 2.0 wt. % gallium is associated with the catalyst.

EXAMPLES

In the examples, the resulting products were evaluated by a scanning electron microscope (SEM), X-ray diffractometry (XRD), spectroscopy and by measurements of the specific surface area and pore size distribution with krypton or nitrogen adsorption.

Scanning electron microscope studies were conducted on samples coated with gold (by a sputtering technique). A scanning electron microscope of the Philips XL 30 type with a Lanthanum hexa-Boride emission source was used in these studies.

X-ray diffraction studies were conducted with a Siemens D-5000 powder diffractometer.

Nitrogen adsorption measurements to determine specific surface area and particle size distribution were carried out with an ASAP 2010 from Micromeritics Instruments, Inc.

Elemental analysis concerning carbon, nitrogen and hydrogen was carried out on certain samples by means of an analytical instrument from LECO Corporation (LECO CHN-600). The particle size and particle size distribution for the colloidal suspensions of discrete microcrystals of molecular sieves used as starting material according to the process were determined by dynamic light scattering (Zeta-Plus, Brookhaven Instruments).

Example 1

Macrostructures comprising spherical particles of porous amorphous silica with very high specific surface area were prepared. When loaded with one or more noble metals, the macrostructures may find particular application in reforming and hydrodesulfonation. The preparation of the macrostructure was carried out as follows:

A synthesis solution with the following composition (on a molar basis): $9TPAOH:25SiO_2:480H_2O:100EtOH$ (TPAOH representing tetrapropylammonium hydroxide and EtOH representing ethanol) was prepared by mixing 20.0 grams of tetraethoxysilane (>98%), 34.56 grams of tetrapropylammonium hydroxide (1.0M solution) and 5.65 grams of distilled water. The mixture was allowed to hydrolyze in a polyethylene flask on a shaking table for 12 hours at room temperature. An amount of 1.0 grams of a strongly basic anion exchange resin sold under the tradename Dowex 1X2-100 type and manufactured by the Dow Chemical Company was added to 10 grams of the synthesis solution. The anion exchange resin was present as spherical particles with a particle size range of 50–100 mesh (dry) and the ion exchange capacity of the resin was specified by the manufacturer to be 3.5 mEq/g.

The mixture of ion exchanger and synthesis solution was heated in a polyethylene reactor equipped with a reflux condenser in an oil bath at 100° C. for 48 hours. After this time, the ion exchanger resin particles were separated from the solution by filtration and treated in a 0.1M ammonia solution in an ultrasound bath for 15 minutes and then separated from the ammonia solution by filtration. Next, the particles were washed three times in distilled water, followed by separation by filtration, and then dried in a heating cabinet at 60° C. for 12 hours. Next, the particles were calcined at 600° C. in air for 4 hours, after heating to this temperature at a rate of 10° C./min.

The resulting material consisted of hard, solid, white spherical particles with a size distribution identical to that in the employed ion exchanger. Elemental analysis showed that the particles were almost entirely free of carbon, hydrogen and nitrogen, which showed that the ion exchanger had been completely eliminated in the calcining stage.

Figure 2:
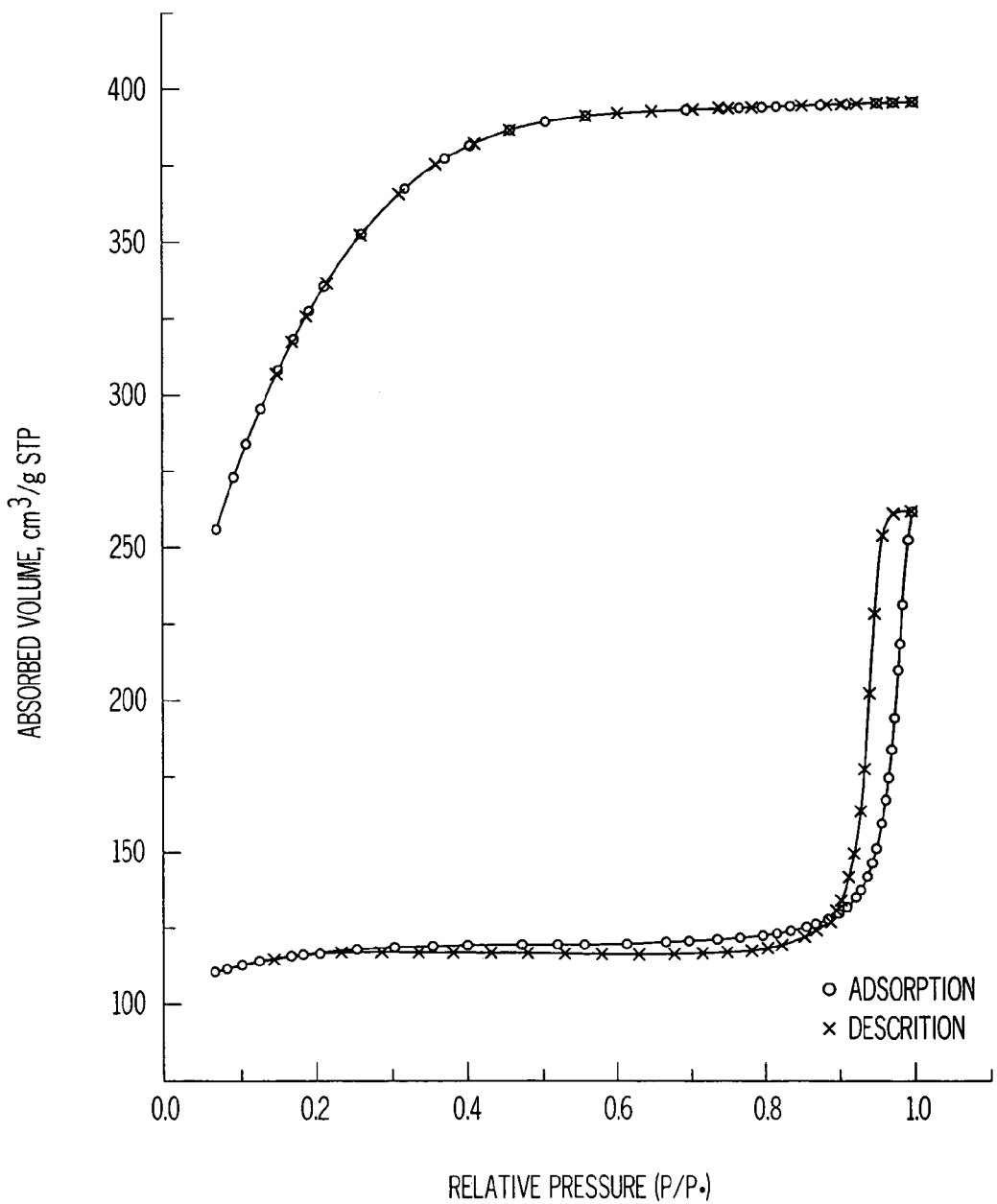
FIG. 2 represents adsorption-desorption isotherms measured for spherical particles of amorphous silica of Examples 1 and 2.

X-ray diffractometry also showed that the material was completely amorphous. The particles were also analyzed by nitrogen adsorption measurements at the boiling point of nitrogen to determine the specific surface area, the adsorption isotherm and pore size distribution of the porous amorphous silica. The specific surface area was calculated from the adsorption data according to the BET equation as 1220 m²/g. The recorded isotherm is shown in FIG. 2 and was of type I, which is typical of porous materials. Calculation of the pore size distribution by the BJH method (desorption isotherm) showed that a very small fraction (about 20 m²/g) of the total specific surface area of the material was found in pores in the mesopore range (diameter >20 Å). The average pore diameter was calculated at 9.5 Å by the Horvath-Kawazoes method.

Example 2

Macrostructures comprising spherical particles of porous amorphous aluminum silicate with very high specific surface area were prepared. When loaded with one or more noble metals, the macrostructures may find particular application in reforming, hydrodesulfonation, and dehydrogenation. The preparation of the macrostructures were carried out as follows:

25 grams of a synthesis solution with the molar composition: $2.4Na_2O:1.0TEACl:0.4Al_2O_3:10SiO_2:/460H_2O$ (TEACl representing tetraethylammonium chloride) were added to 2.0 grams of a strongly basic ion exchanger sold under the tradename Dowex MSA-1 and manufactured by the Dow Chemical Company (particle size 20–50 mesh and [dry] ion exchange capacity of 4 mEq/g) in a polyethylene reactor. The synthesis mixture was prepared by first dissolving 0.75 grams sodium aluminate (50.6 wt. % $Al_2O_3$, 36 wt. % $Na_2O$) in 35 grams of a 1M NaOH solution at 100° C. This solution was then added to a mixture of 40 grams distilled water, 1.66 grams TEACl and 15 grams silica sol (Bindzil 40/130, Eka Chemicals AB, solids content 41.36 wt %, 0.256 wt % $Na_2O$) during agitation for 2 hours. The mixture of ion exchanger and synthesis solution was treated in a polyethylene reactor equipped with a reflux condenser in an oil bath at 100° C. for 48 hours. After this time, the ion exchanger particles were separated from the solution by filtration and treated in a 0.1M ammonia solution in an ultrasound bath for 15 minutes and then separated from the ammonia solution by filtration. The particles were finally washed three times by suspension in distilled water, followed by separation by filtration, and then dried in a heating cabinet at 60° C. for hours. Next, the particles were calcined at 600° C. in air for 4 hours, after heating to this temperature at a rate of 10° C./min.

Visual inspection and analysis with a scanning electron microscope showed that the resulting material consisted of very hard, solid, white spherical particles with size distribution identical to that in the employed ion exchanger. Elemental analysis showed that the particles were almost entirely free of carbon, hydrogen and nitrogen, which showed that the ion exchanger material had been completely eliminated in the calcining stage.

X-ray diffractometry showed that the material was completely amorphous. The particles were further analyzed by nitrogen adsorption measurements at the boiling point of nitrogen to determine the specific surface area, adsorption isotherms and pore size distribution. The specific surface area was calculated from the adsorption data according to the BET equation as 594 $m^2/g$. The recorded isotherm is shown in Example 2 and was of type IV. Calculation of the pore size distribution by the BJH method (desorption isotherm) showed that a relatively large percentage of the total (cumulative) pore volume (about 65%) was found in pores in the mesopore range (radius >20 Å).

Example 3

Macrostructures comprising spherical particles of silicalite 1. These macrostructures may find particular application in xylenes isomerization and hydrocarbon separation. The preparation of the macrostructures were carried out as follows:

14.3 grams of a synthesis solution with the molar composition: $9TPAOH:25SiO_2:480H_2O:100EtOH$ were added to 1.0 grams of a macroporous strongly basic ion exchanger sold under the tradename Dowex MSA-1 and manufactured by the Dow Chemical Company (particle size 20–50 mesh [dry]; ion exchange capacity: 4 mEq/g). The synthesis mixture was prepared as described in Example 1. The mixture of ion exchanger and synthesis solution was heated in a polyethylene reactor equipped with a reflux condenser in an oil bath at 100° C. for 48 hours. After this time, the ion exchanger particles were separated from the solution and the material was crystallized in the bulk phase by filtration and treated in a 0.1M ammonia solution in an ultrasound bath for 15 minutes, whereupon they were separated again by filtration. Next, the particles were washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Figure 3:
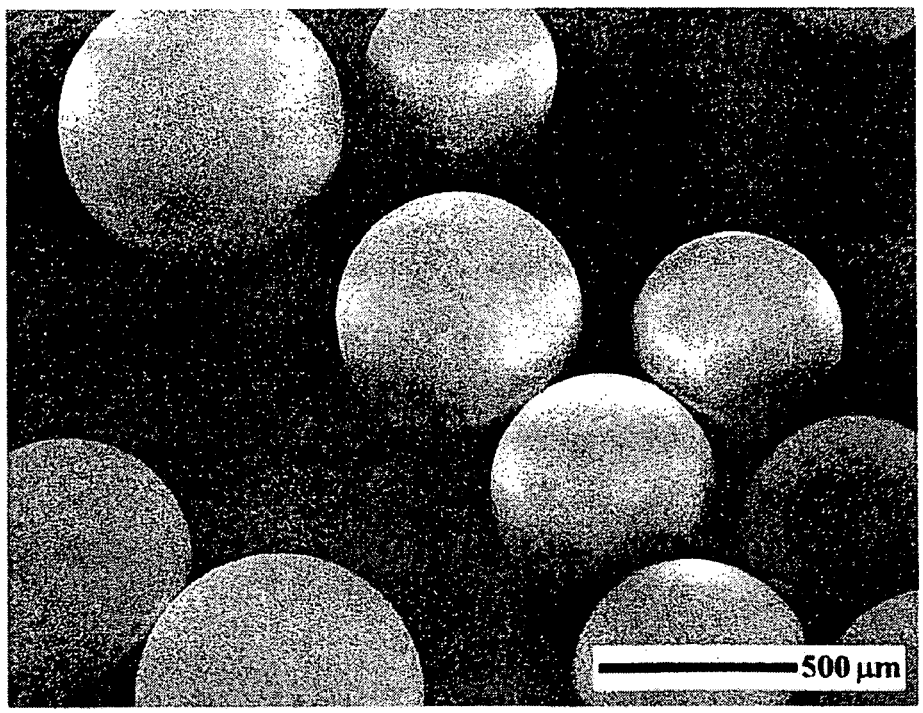
FIG. 3 and FIG. 4 represents SEM micrographs, at two different magnifications, of spherical particles of the silicalite 1 of Example 3.
Figure 4:
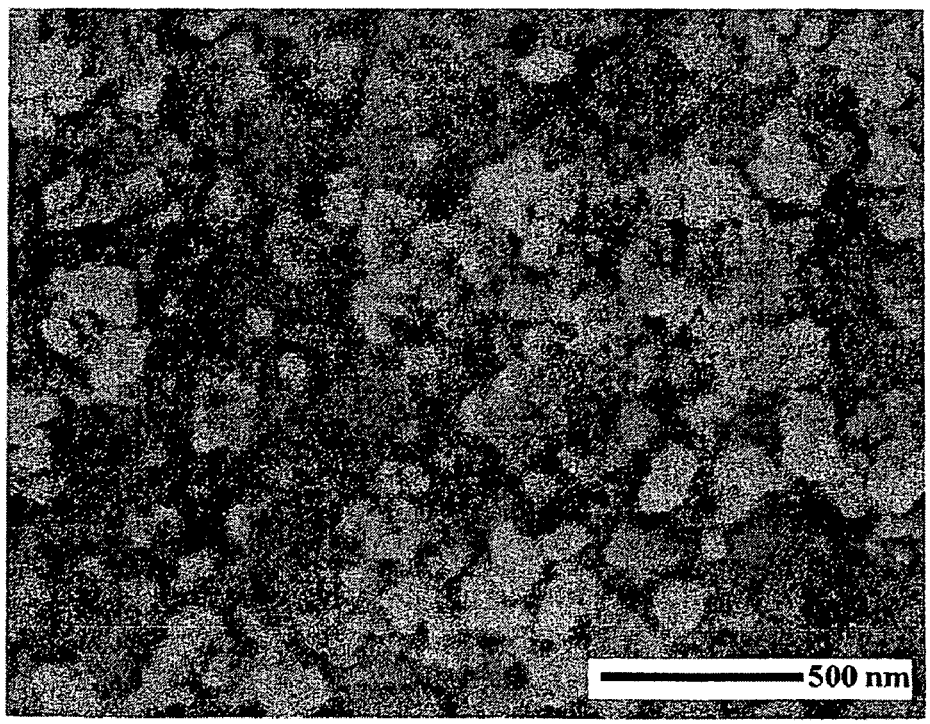
Figure 5:
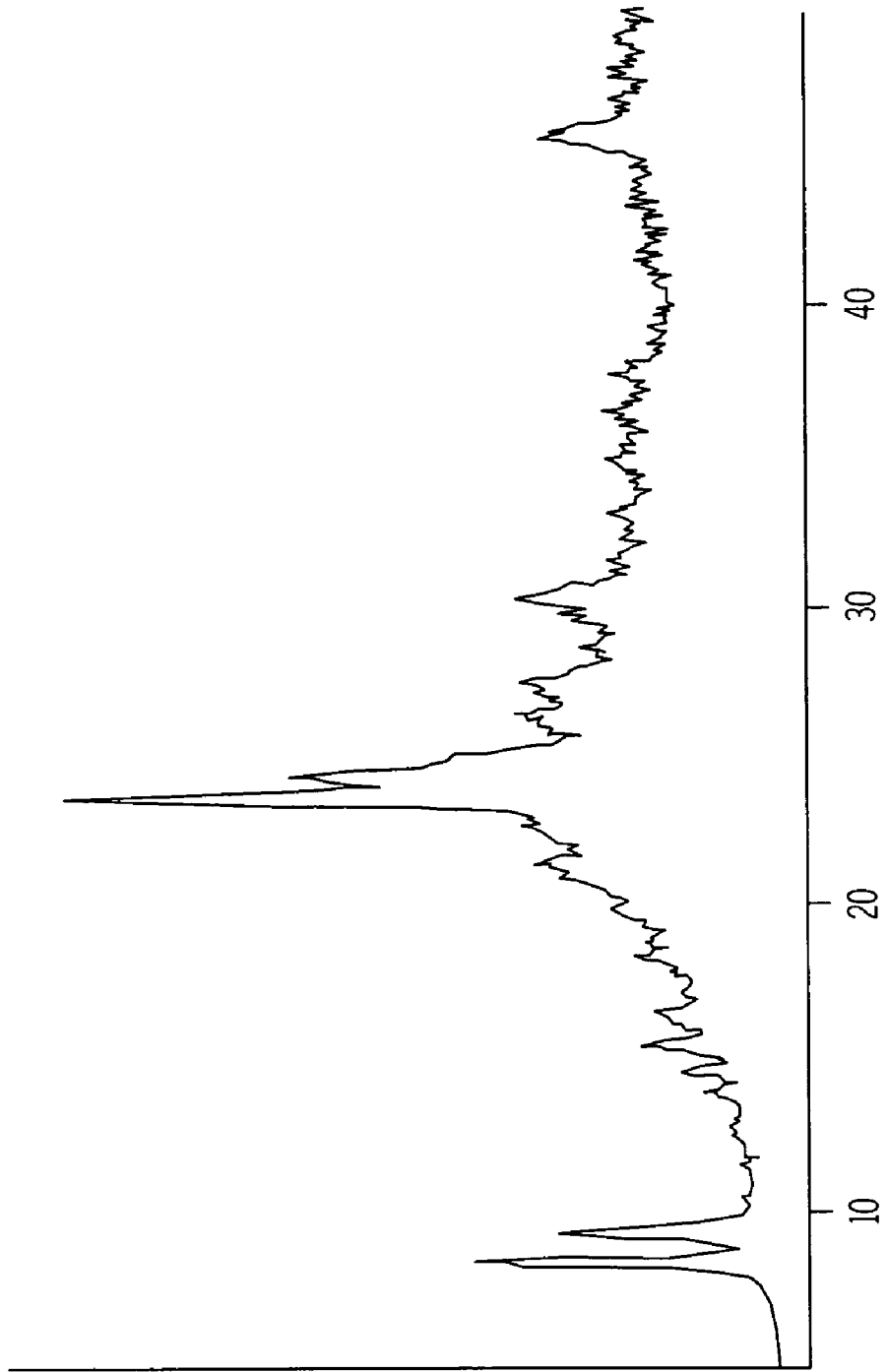
FIG. 5 represents an X-ray diffraction pattern for spherical particles of the silicalite 1 of Example 3.

Visual inspection and scanning electron microscopy revealed that the resulting material consisted of very hard, solid (homogeneous), white spherical particles with a size distribution identical to that in the employed ion exchanger. The primary particles making up the spheres had a size of about 100 nm. Also, the primary particles on the surface of the spheres was similar to the particles in the interior of the spheres. Elemental analysis showed that the particles were almost entirely free of carbon, hydrogen and nitrogen, which showed that the ion exchanger material was fully eliminated in the calcining stage. FIGS. 3 and 4 are two SEM photographs of the material taken at two different magnifications. FIG. 3 taken at the lower magnification shows the spherical character of the particles, whereas FIG. 4 taken at high magnification shows the presence of small primary particles (primary crystals) with a size of about 100 nm. X-ray diffractometry revealed that the material is crystalline and consists of silicalite 1, but that it also contains a percentage of amorphous material. An X-ray diffraction pattern for this sample is shown in FIG. 5. Analysis with nitrogen adsorption gave a specific surface area of 438 $m^2/g$ and showed that most of the pore volume was found in micropores with an average pore diameter of 6 Å, calculated according to the Horvath-Kawazoes method.

Silicalite 1 was prepared using the same procedures as described above, except that the hydrothermal treatment was carried out at different temperatures.

In the first silicalite 1 preparation, the hydrothermal treatment temperature was 165° C. Scanning electron microscopy showed that the surface of the spheres of the resulting product were built up with crystals of MFI-type zeolite and had a size up to 500 nm. The inner part of the spheres was less homogeneous and agglomerates of small particles could be distinguished.

In the second preparation, the hydrothermal treatment was carried out in two steps. The temperature of the first step was 100° C. and the temperature of the second step were at 165° C. The resulting spheres were highly crystalline which indicates that the degree of crystallinity can be increased by a second hydrothermal treatment at a higher temperature.

Example 4

Macrostructures comprising spherical particles of ZSM-5 were prepared as follows:

15 grams of a synthesis solution with the molar composition: $0.35\ Na_2O:9TPAOH:0.25Al_2O_3:25\ SiO_2:405\ H_2O$ were added to 1.0 grams of a macroporous strongly basic anion exchanger sold under the tradename Dowex MSA-1 and manufactured by the Dow Chemical Company (particle size 20–50 mesh [dry]; ion exchange capacity: 4 mEq/g). The synthesis mixture was prepared by first dissolving 0.408 grams of aluminum isopropoxide in 10 grams of 1.0M tetrapropylammonium hydroxide. Another solution was prepared by dissolving 6.0 grams freeze-dried silica sol (Bindzil 30/220, 31 wt % $SiO_2$, 0.5 wt % $Na_2O$ Eka Chemicals, AB) in 26 grams 1.0M TPAOH at 100° C. The two solutions were mixed under agitation for 30 minutes. The mixture of ion exchanger and synthesis solution was heated in a polyethylene reactor equipped with a reflux condenser in an oil bath at 100° C. for 20 days. After this time, the ion exchanger particles were separated from the solution and the material was crystallized in the bulk phase by filtration and treated in a 0.1M ammonia solution in an ultrasound bath for 15 minutes, and then separated again by filtration. Next, the particles were washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Visual inspection and analysis with a scanning electron microscope showed that the product largely consisted of white, solid particles with a size and shape identical to that of the employed ion exchanger. A relatively large fraction of the product, however, was shown to consist of particles with roughly the same size as the employed ion exchanger, but with a more irregular shape. SEM analysis at high magnification showed that the particles consisted of intergrown crystals with a morphology typical of MFI structures and with a size of about 1 µm. X-ray diffractometry showed that the particles consisted of ZSM-5 and a relatively large fraction of amorphous material. The specific surface area was measured by nitrogen adsorption at 612 $m^2/g$.

Example 5

Macrostructures comprising spherical particles of zeolite A. These macrostructures may find particular application in the isomerization of linear paraffins. The preparation of the macrostructures was carried out as follows:

Macrostructure comprising spherical particles of were prepared as follows:

18.0 grams of a synthesis solution with the molar composition: 0.22 $Na_2O$:5.0 $SiO_2$:$Al_2O_3$:8 $TMA_2O$:/400 $H_2O$ were added to 1.0 grams of a strongly basic anion exchanger sold under the tradename Dowex MSA-1 and manufactured by the Dow Chemical Company. The synthesis mixture was prepared by first dissolving 1.25 grams of aluminum isopropoxide and 9.0 grams tetramethylammonium hydroxide pentahydrate in 0.90 grams of 1.0M solution of NaOH and 3.0 grams water under agitation for 2 hours. This solution was added to a mixture of 3.0 grams silica sol (Bindzil 30/220, 31 wt % $SiO_2$, 0.5 wt % $Na_2O$ Eka Chemicals, AB) and 12 grams of distilled water and the resulting solution was agitated for 3 hours. The mixture of ion exchanger and synthesis solution was heated in a polyethylene reactor equipped with a reflux condenser in an oil bath at 100° C. for 10 hours. After this time, the ion exchanger particles were separated from the solution and the material was crystallized in the bulk phase by filtration and treated in a 0.1M ammonia solution in an ultrasound bath for 15 minutes, and then separated again by filtration. Next, the particles were washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Visual inspection and analysis by scanning electron microscopy showed that the product largely consisted of light brown, solid particles with a size and shape identical to that of the employed ion exchanger. A smaller fraction of the product consisted of fragmented particles. SEM at high magnification showed that the particles are homogeneous and are constructed from intergrown primary particles with a size up to about 300 nm. X-ray diffractometry showed that the resulting material contained zeolite A and a certain amount of amorphous material. Nitrogen adsorption measurements gave a specific surface area (according to the BET equation) of 306 $m^2/g$ and indicated the presence of both micro- and mesoporosity.

Example 6

Macrostructures comprising spherical particles of zeolite Beta were prepared as follows:

15 grams of a synthesis solution with the molar composition: 0.35 $Na_2O$:9TEAOH:0.5$Al_2O_3$:25 $SiO_2$:295 $H_2O$ were added to 1.0 grams of a strongly basic anion exchanger sold under the tradename Dowex MSA-1 and manufactured by the Dow Chemical Company. The synthesis mixture was prepared by dissolving 0.81 grams aluminum isopropoxide in 6.0 grams tetraethylammonium hydroxide TEAOH, 20% solution) at 100° C. This solution was added to a solution of 6.0 grams freeze-dried silica sol (Bindzil 30/220, 31 wt % $SiO_2$, 0.5 wt % $Na_2O$ Eka Chemicals, AB) dissolved in 20 grams of TEAOH (20% solution) and the resulting solution was agitated for 30 minutes. The mixture of ion exchanger and synthesis solution was heated in a polyethylene reactor equipped with a reflux condenser in an oil bath at 100° C. for 8 days. After this time, the ion exchanger particles were separated from the solution and the material was crystallized in the bulk phase by filtration and treated in a 0.1M ammonia solution in an ultrasound bath for 15 minutes, whereupon the particles were separated again by filtration. The particles were finally washed three times by suspension in distilled water, followed by separation by filtration, and then dried in a heating cabinet at 60° C. for 12 hours. Next, the particles were calcined at 600° C. in air for 10 hours, after heating to this temperature at a rate of 1° C./min.

Visual inspection, as well as analysis with a scanning electron microscope, showed that the product largely consisted of hard, white, solid particles with a size and shape identical to that of the employed ion exchanger. SEM analysis at high magnification shows that the material is constructed of intergrown primary particles with a size of about 80 nm. X-ray diffractometry showed that the particles contained zeolite Beta as the only crystalline phase. The specific surface area calculated with the BET equation, based on nitrogen adsorption data, was 580 $m^2/g$.

Example 7

A film of silicalite 1 was built upon the surface of a macrostructure of silicalite 1 produced according to Example 3 as follows:

10.0 grams of synthesis solution with the composition and preparation according to Example 3 were added to 0.20 grams of calcined product produced according to Example 3. This mixture was heated at 100° C. in a polyethylene reactor equipped with a reflux condenser for 48 hours. After this time, the particles were separated from the solution and the material was crystallized in the bulk phase by filtration and treated in a 0.1M ammonia solution in an ultrasound bath for 15 minutes, whereupon they were separated again by filtration. The particles were finally washed three times by suspension in distilled water, followed by separation by filtration, and then dried in a heating cabinet at 60° C. for 12 hours. Part of the material was calcined at 600° C. for 10 hours, after heating to this temperature at a rate of 1° C./min.

X-ray diffraction measurements on the calcined sample revealed that the sample contained silicalite 1 as the only crystalline phase. Scanning electron microscopy detected an outer layer of silicalite 1 on the surface of the particles, a layer that synthesis had built up from about 300/-nm large primary particles. The specific surface area was determined for the uncalcined sample as 92 m$^2$/g, whereas the corresponding value measured for the calcined sample was 543 m$^2$/g. The difference in the surface before and after calcining indicates that the outer shell of silicalite 1 effectively encloses the open pore system in the original particles.

Example 8

Macrostructure of ZSM-5 having a surface coating of silicalite 1 were produced as follows:

20 grams of a synthesis solution with the molar composition: 0.31 Na$_2$O:9TPAOH:0.25Al$_2$O$_3$:25 SiO$_2$:405 H$_2$O were added to 2.0 grams of a macroporous strongly basic anion exchanger sold under the tradename Dowex MSA-2 and manufactured by the Dow Chemical Company. The mixture of ion exchanger and synthesis solution was aged for one hour at room temperature and then heated in a polyethylene reactor equipped with a reflux condenser in an oil bath at 170° C. for 17 hours. After this time, the ion exchanger particles were separated from the solution and the material was crystallized in the bulk phase by filtration and treated in a 0.1M ammonia solution in an ultrasound bath for 5 minutes, and then separated again by filtration. Next, the particles were washed several times by suspension in distilled water, followed by separation by filtration, and then dried in a heating cabinet at 60° C. Next, the particles were calcined at 600° C. in air for 5 hours, after heating to this temperature at a rate of 1° C./min.

XRD analysis of the product indicated highly crystalline ZSM-5 having a spherical shape.

1.2 grams of the product were placed into a polyethylene reactor and then 20 grams of a synthesis solution with the molar composition: 3TPAOH:25 SiO$_2$:404H$_2$O:100EtOH were added to the reactor. The mixture of product and synthesis solution were preheated to 100° C. and heating continued at this temperature in the polyethylene reactor which was equipped with a reflux condenser for 48 hours. After this time, the coated macrostructures were separated from the Silicalite which had crystallized in bulk, and treated in a 0.1M ammonia solution in an ultrasound bath for 5 minutes. The particles were washed several times by distilled water and then dried in a heating cabinet at 60° C. Next, the particles were calcined at 600° C. in air for 5 hours, after heating to this temperature at a rate of 1° C./min to remove the TPA cations.

Figure 6:
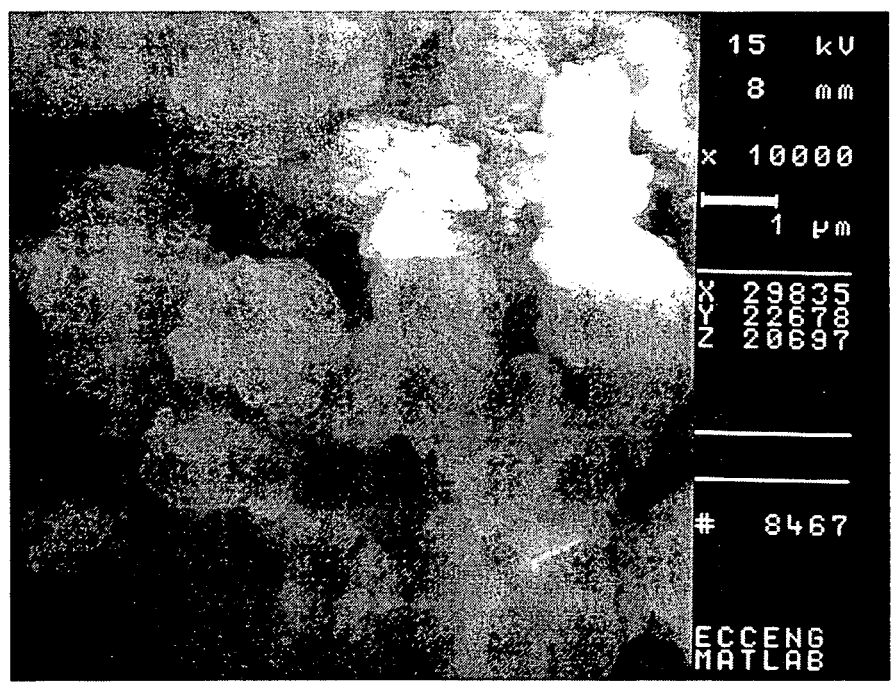
FIG. 6 represents a SEM micrograph of the macrostructure of Example 8.
Figure 7:
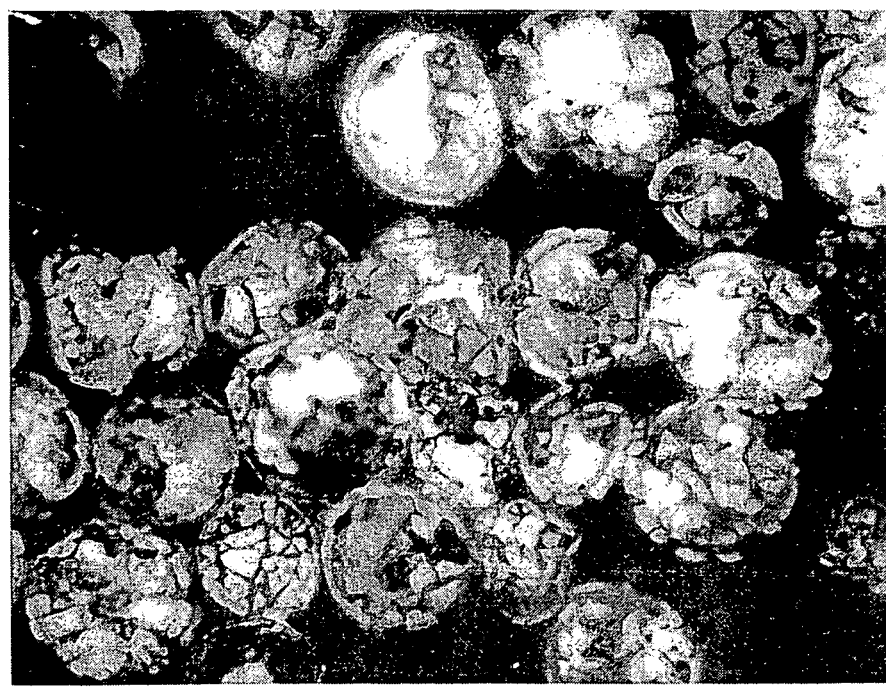
FIG. 7 represents a photographic image with magnification of 25 times of a cross section of the macrostructure of Example 8.

Visual inspection, as well as analysis showed that the product largely consisted of hard, white, solid particles. SEM analysis (FIG. 6) showed the presence of crystals of less than 0.5 micron coating 2 micron particles of the macrostructures. FIG. 7 shows the mesopores and macropores of the macrostructure. ICP analysis of the macrostructure determined the silica to alumina mole ratio to be 80.

The density of the macrostructure was determined to be 0.38 g/cc.

Example 9

I. Preparation of Macrostructures Comprising Crystals of Zeolite Beta.

10 grams of a synthesis solution with the molar composition: 0.31 Na$_2$O:9TEAOH:0.5Al$_2$O$_3$:25 SiO$_2$:295 H$_2$O were added to 1.0 grams of a strongly basic anion exchanger sold under the tradename Dowex MSA-1. The mixture of ion exchanger and synthesis solution were heated in a polyethylene reactor equipped with a reflux condenser in an oil bath at 170° C. for 24 hours. After-this time, the ion exchanger particles were separated from the solution and the material was crystallized in the bulk phase by filtration and treated in a 0.1M ammonia solution in an ultrasound bath for 5 minutes, whereupon the particles were separated again by filtration. The particles were finally washed several times by suspension in distilled water, followed by separation by filtration, and then dried in a heating cabinet at 60° C. for 12 hours. Next, the particles were calcined at 600° C. in air for 5 hours, after heating to this temperature at a rate of 1° C./min.

Visual inspection, as well as analysis showed that the product largely consisted of hard, white, solid particles with a size and shape identical to that of the employed ion exchanger. ICP analysis of the macrostructure determined the silica to alumina mole ratio to be 25.

II. Test of the Macrostructures comprising zeolite Beta in the Disproportionation of Cumene The macrostructures prepared according to Part I above were tested in the disproportionation of cumene.

The test was carried out by first packing fifty milligrams of 40–60 mesh catalyst in a stainless steel reactor. The macrostructures were pretreated at 450° C. with N$_2$ for two hours. Next, the macrostructures were contacted by co-feed of cumene and nitrogen. Total pressure of reaction was controlled at 54 psia. The partial pressure of the cumene feed was 13.5 psia and partial pressure of N$_2$ feed was 40.5 psia. Cumene flowrate was 15.43 µl/min. The nitrogen stream was controlled by a Brooks mass flow controller and the cumene feed stream was pumped by a syringe pump. The temperature used in the tests ranged from 225 to 300° C. All products were analyzed by an on-line HP 6890 GC equipped with a Chirasil DEX CP column. The catalyst performance was:

| | |
|---|---|
| Cumene Conversion: | 15–20% |
| Bz Selectivity: | 40% |
| DIPB Selectivity: | 50% |

The results show very high disproportionation conversion. The high diisopropylbenzene (DIPB) yield demonstrates high activity of the zeolite beta in the macrostructure.

Example 10

Preparation of Catalyst A—Macrostructures comprising crystals ZSM-5

30 grams of a synthesis solution with the molar composition: 0.31 Na$_2$O:9TPAOH:0.25Al$_2$O$_3$:25 SiO$_2$:405 H$_2$O were added to 2.0 grams of a macroporous strongly basic anion exchanger sold under the tradename Dowex MSA-1. The mixture of ion exchanger and synthesis solution was aged for one hour at room temperature and then heated in a polyethylene reactor equipped with a reflux condenser in an oil bath at 170° C. for 24 hours. After this time, the ion exchanger particles were separated from the solution and the material was crystallized in the bulk phase by filtration and treated in a 0.1M ammonia solution in an ultrasound bath for 5 minutes, and then separated again by filtration. Next, the particles were washed several times by suspension in distilled water, followed by separation by filtration, and then dried in a heating cabinet at 60° C. for hours. Next, the particles were calcined at 600° C. in air for 5 hours, after heating to this temperature at a rate of 1° C./min.

Visual inspection as well as analysis showed that the product largely consisted of white, solid particles with a size and shape identical to that of the employed ion exchanger. ICP analysis of the macrostructure showed a silica to alumina mole ratio of 49.

Preparation of Catalyst B—Macrostructures Comprising Crystals of ZSM-5

Catalyst B was prepared the same as Catalyst A.

Visual inspection as well as analysis showed that the product largely consisted of white, solid particles with a size and shape identical to that of the employed ion exchanger. The silica to alumina mole ratio of the ZSM-5 was 44.

Separate tests were carried out using Catalysts A and B in the disproportionation of cumene. To compare the performance of these Catalysts, a prior art ZSM-5 catalyst was also tested in the disproportionation of cumene. The ZSM-5 catalyst comprised of crystals having sizes in the range of from 0.2 to 1.0 micron had a silica to alumina mole ratio of 34. The tests used the same conditions and procedures described in Section II of Example 9. The results of these tests are shown in Table I below.

TABLE I

|  | Catalyst A | Catalyst B | Prior Art ZSM-5 |
|---|---|---|---|
| Cumene Conversion (%) | 30–60 | 40–50 | 10–20 |
| Bz Selectivity (%) | 95 | 90 | 80 |
| DIPB Selectivity (%) | 5 | 5 | 2 |

The results of these tests show that Catalysts A and B were more active in the disproportionation of cumene than the prior art ZSM-5 catalyst.

Example 11

Sample A was tested for xylene isomerization and ethylbenzene dealkylation. The test was carried out by first packing fifty milligrams of 40–60 mesh catalyst in a stainless steel reactor. The catalyst was retreated at 450° C. with $H_2$ for two hours followed by co-feed of 50:50 molar ethylbenzene:m-xylene and hydrogen. Total pressure of reaction was controlled at 54 psia. The partial pressure of ethylbenzene feed was 3.4 psia, partial pressure of m-xylene feed was 3.4 psia, and partial pressure of $H_2$ feed was 47.2 psia. Hydrocarbon flowrate was 7.7 μl/min. The hydrogen stream was controlled by a Brooks mass flow controller and the hydrocarbon feed stream was pumped by a syringe pump. The temperature investigated in the tests ranged from 200 to 500° C. All products were analyzed by an on-line HP 6890 GC equipped with a Chirasil DEX CP column. The results of these tests are shown in Tables below.

TABLE II

|  | 200° C. | 300° C. | 400° C. | 500° C. |
|---|---|---|---|---|
| Ethylbenzene Conversion (%) | 0.2 | 2.4 | 20.6 | 34.3 |
| % of reacted ethylbenzene disproportionated | 100 | 100 | 24 | 3.3 |
| % of reacted ethylbenzene dealkylated | 0 | 0 | 76 | 96.7 |

TABLE II-continued

|  | 200° C. | 300° C. | 400° C. | 500° C. |
|---|---|---|---|---|
| m-xylene conversion (%) | 2 | 26 | 42 | 43.3 |
| pX:mX:oX | 1.2:98:0.7 | 18:74:8 | 25:58:17 | 25.3:56.7:18 |

At low temperature (200–300° C.), ethylbenzene disproportionation is major reaction pathway. At high temperature, most of the ethylbenzene cracks into ethene and benzene. At 400° C. and above, the catalyst became very effective in isomerizating mX to pX.

What is claimed is:

1. A catalyst suitable for hydrocarbon conversion, said catalyst comprising:
   (i) at least one macrostructure having a three dimensional network of self supporting and self bound particles comprising a first porous inorganic material, said particles (a) having an average particle size of less than about 2 microns; (b) occupying less than 75% of the total volume of said at least one macrostructure; and (c) being joined together to form a three-dimensional interconnected network comprised of pores having diameters greater than about 20 Å, and
   (ii) a coating comprised of a second porous inorganic material and covering at least a portion of the external surface of said at least one macrostructure,
wherein said first porous inorganic material and said second porous inorganic material are crystalline microporous molecular sieve, and said first porous inorganic material has a composition, or composition structure type, that is different from the composition, or composition structure type, of said second porous inorganic material.

2. The catalyst recited in claim 1, wherein said first porous inorganic material and said second porous inorganic material each have either a large pore size or intermediate pore size.

3. The catalyst recited in claim 1, wherein the structure type of said first porous inorganic material and said second porous inorganic material are selected from the group consisting of MAZ, *BEA, MFI, MEL, MTW, EMT, MTT, HEU, FER, TON, EUO, and ETS-10.

4. The catalyst recited in claim 1, wherein said first porous inorganic material has lower acidity than said second porous inorganic material.

5. The catalyst recited in claim 1, wherein said first porous inorganic material has higher acidity than said second porous inorganic material.

6. The catalyst recited in claim 1, wherein said first porous inorganic material and said second porous inorganic material are each either gallosilicate or aluminosilicate.

7. The catalyst recited in claim 1, wherein said catalyst further comprises at least one catalytically active metal.

8. The catalyst recited in claim 1, wherein said coating substantially covers the external surface of said at least one macrostructure.

9. The catalyst recited in claim 1, wherein the structure type of said first porous inorganic material and said second porous inorganic material are each either MFI or MEL.

10. The catalyst recited in claim 1, wherein said first porous inorganic material is ZSM-5 and said second porous inorganic material is silicalite 1 or silicalite 2.

* * * * *